United States Patent [19]

Garde

[11] Patent Number: 5,260,218
[45] Date of Patent: Nov. 9, 1993

[54] AUTOCLAVE CORROSION TEST FOR ZIRCONIUM ALLOYS

[75] Inventor: Anand M. Garde, Simsbury, Conn.

[73] Assignee: Combustion Engineering, Inc., Windsor, Conn.

[21] Appl. No.: 604,738

[22] Filed: Oct. 29, 1990

[51] Int. Cl.[5] ............... G01N 31/00; G01N 17/00; G21C 17/00
[52] U.S. Cl. ........................... 436/6; 422/53; 73/865.6; 376/250; 376/251
[58] Field of Search ............... 422/53; 436/6; 73/61.2, 73/865.6; 376/250, 251

[56] References Cited

U.S. PATENT DOCUMENTS

| | | | |
|---|---|---|---|
| 4,267,148 | 5/1981 | Dickson et al. | 436/6 |
| 4,643,866 | 2/1987 | Thornton et al. | 376/251 |
| 4,688,638 | 8/1987 | Williams | 436/6 |
| 4,916,076 | 4/1990 | Johnson, Jr. et al. | 436/6 |

OTHER PUBLICATIONS

"Review of Corrosion and Dimensional Behavior of Zircaloy under Water Reactor Conditions", Zirconium in the Nuclear Industry (4th Conf) ASTM STP 1979. pp. 91–106.
Chirigos et al, "The Mechanism of Oxidation and Corrosion of Zirconium", Proc. AEC Metallurgy Conf., Mar. 1952, p. 337, Report TIP-5084.
Thomas, "Corrosion of Zirconium and Its Alloys in Water and Steam", *The Metallurgy of Zirconium*, Lushman et al, Eds., McGraw-Hill, 1955, p. 622.
Kearns, "Terminal Solubility and Partitioning of Hydrogen in the Alpha-Phase of Zirconium, Zircaloy-2 and Zircaloy-4", *J. Nucl. Mater.* 22, 1967, p. 292.
Douglass, *The Metallurgy of Zirconium*, IAEA Supplement 1971, International Atomic Energy, Vienna, 1971, p. 160.
Newman, "The Hot-cell Examination of Oconee-1 Fuel Rods After Five Cycles of Irradiation", Babcock and Wilcox Report BAW-1874, DOE/ET/34212-59 Oct. 1986.
Garzarolli et al, "Behavior of Core Structural Materials in Light Water Cooled Power Reactors", IAEA-S-M-288/24, *Proceedings of the IAEA Symposium on Improvements in Water Reactors Fuel Technology and Utilization*, Stockholm, Sweden, Sep. 1986, International Atomic Energy Agency, Vienna, 1987. pp. 387–407.
Schemel, "New Heat Treatment Cuts Zircalot-2 Corrosion, Hydrogen Embrittlement", Nucleonics, vol. 21, No. 11, Nov. 1963.
Sabol et al, "Development of a Cladding Alloy for High Burnup", *Zirconium in the Nuclear Industry: 8th International Symposium*, ASTM STP 1023, Philadelphia, 1989. pp. 227–244.
Ploc, "Oxidation Kinetics and Auger Microprobe Analysis of Some Oxidized Zirconium Alloys", Zirconium in the Nuclear Industry: 8th International Symposium, ASTM, STP 1023, Philadelphia, 1989. pp. 498–514.
Peters, "Improved Characterization of Aqueous Corrosion Kinetics of Zircaloy-4", *Zirconium in the Nuclear Industry: 6th International Symposium*, ASTM STP 824, 1984. pp. 507–518.

(List continued on next page.)

Primary Examiner—Robert J. Warden
Assistant Examiner—Christopher Y. Kim
Attorney, Agent, or Firm—John H. Mulholland

[57] ABSTRACT

An improved short-term autoclave (10) test for ex-reactor evaluation of in-reactor corrosion resistance of zirconium alloy members (16) for use in pressurized water reactors and pressurized heavy water reactors by:
  providing a heat flux to initiate hydride precipitation close to the metal-oxide interface of the tube outside surface by means of a resistance heater (20) and a directed flow of aqueous coolant in the water phase to only the outside surface which is one of two specimen (16) opposed surfaces; providing the inside surface with access to the coolant from the flow but not in the flow; reducing the distance between the opposed surfaces of specimen (16);
  regulating coolant flow from inlet port (12) to outlet port (14) and power of autoclave (10) to optimum saturation condition of 360° C.±5° C. and pressure 2700 p.s.i.±100 p.s.i.;
  providing a coolant chemistry which simulates a rector's;
  removing most of the oxygen from the coolant.

11 Claims, 1 Drawing Sheet

OTHER PUBLICATIONS

Garde, "Hot-cell Examination of Extended Burnup Fuel from Fort Calhoun" Combustion Engineering Report CEND-427, DOE/ET/34030-11, Sep. 1986.

Billot, et al., "Development of a Mechanistic Model to Assess the External Corrosion", *Zirconium in the Nuclear Industry: 8th International Symposium;* ASTM STP 1023, Philadelphia, 1989. pp. 165-184.

Schemel et al, "Influence of the Manufacturing Process on the Corrosion Resistance of Zircaloy-4 Cladding", Zirconium in the Nuclear Industry: 8th Int'l Symposium, ASTM STP 1023, Philadelphia, 1989. pp. 141-152.

Corsetti et al, "ABB-CE Experience With High Burnup Fuel Performance". IAEA Tech. Comm. Meeting on Fuel Performance at High Burnup for Water Reactors., Nykoeping, Sweden, Jun. 5-8, 1990.

Cox, "What Is Wrong with Current Models for In-reactor Corrosion", IAEA Meeting on Fundamental Aspects of Corrosion of Zirconium Base Alloys in Water Reactor Environments, Portland, Oreg. 1989.

Lanning et al, "Corrosion and Hydriding of N Reactor Pressure Tubes", *Zirconium in the Nuclear Industry: 8th Int'l Symposium,* ASTM STP 1023, Philadelphia, 1989 pp. 3-19.

Urbanic et al, "Long-term Corrosion and Deuterium Uptake in CANDV-PHW Pressure Tubes", *Zirconium in the Nuclear Industry: 7th Int'l Symposium,* ASTM STP 939, Philadelphia, 1987, pp. 189-205.

Hillner, "Long-term In-reactor Corrosion and Hydriding of Zircaloy-2 Tubing", *Zirconium in the Nuclear Industry: 5th Conference,* ASTM STP 754, Philadelphia, 1982 pp. 450-478.

Kilp et al, "Improvements in Zirconium Alloy Corrosion Resistance", IAEA Meeting on Fundamental Aspects of Corrosion of Zirconium-based Alloys in Water Reactor Environments, Portland, Oreg., Sep. 11-15, 1989.

Thomazet et al, "Fragema Zirconium Alloy Corrosion Behavior and Development" IAEA Meeting on Fundamental Aspects of Corrosion of Zr-based Alloys in Water Reactor Environments, Portland, Oreg., Sep. 11-15, 1989.

Garde, A. M. "Effect of Irradiation and Hydriding on the Mechanical Properties of Zircaloy-4 at High Fluence", Zirconium in the Nuclear Industry: 8th Int'l Symposium, ASTM STP 1023, Philadelphia, 1989. pp. 548-569.

Kass, "The Development of the Zircaloys", ASTM STP 368. ASTM, 1963.

Northwood et al, "Hydrides and Delayed Hydrogen Cracking in Zirconium and Its Alloys" *International Metal Reviews,* 28. 1983, No. 2.

Johnson, Jr., "Thick Film Effects in the Oxidation and Hydriding of Zirconium Alloys" PNL-SA-17065, IAEA Meeting on Fundamental Aspects of Corrosion of Zirconium Base Alloys in Water Reactor Environments, Portland, Oreg., Sep. 11-15, 1989.

Thomas et al, "Predictionary Computer of Corrosion and Hydriding of Zircaly-4 Under Heat Transfer Conditions", *Trans. ASM.* 58, 1965 p. 658.

Goldman et al, "Hydrogen Pickup During Corrosion on Testing of Zirconium", Report WAPD-MM-184, Feb. 19, 1953.

Parker et al, "Properties of Hydrided Zirconium", USAEC Report APEX-561, General Electric Company, Dec. 1959.

Chung, "Correlation of Waterside Corrosion and Cladding Microstructure in High-burnup Fuel and Gadolinia Rods", IAEA Meeting on Fundamental Aspects of Corrosion of Zirconium Based Alloys in Water Reactor Environments, Portland, Oreg., Sep. 11-15, 1989.

Lunde et al, "Effect of Material and Environmental Variables Localized Corrosion of Zirconium Alloys", *Zirconium in the Nuclear Industry (4th Conference),* ASTM STP 681, 1979, pp. 40-59.

Bentley, TRG Report 3001 (S), 1977.

Parfenov, et al, Corrosion of Zirconium and Zirconium Alloys, AEC-tr-6978, Translated by Israel Program for Scientific Translations, Jerusalem, 1969, p. 128.

Burton, *J. Nucl. Materials* 2, No. 1, 1960, p. 62.

Klepfer et al, *Nuclear Metallurgy,* 7, AIME, New York. 1960.

Douglass, *Corrosion,* 17, No. 1, 1961, p. 105.

Chung et al, "High Temperature Oxidation of Zircaloy in Hydrogen-Steam Mixtures", *Zirconium in the Nuclear Industry: 6th Int'l Symposium,* ASTM STP 824, 1984. pp. 793-809.

Garzarolli et al, "Progress in the Knowledge of Nodular Corrosion", *7th Int'l Symposium,* ASTM STP 939, Philadelphia, 1987. pp. 417-430.

Cheng et al, "Development of a Sensitive and Reproducible Steam Test for Zircaloy Nodular Corrosion", *Zirconium in the Nuclear Industry: 7th Int'l Symposium,* ASTM STP 939, Philadelphia, 1987. pp. 257-283.

360°C Aqueous Coolant

AUTOCLAVE CORROSION TEST FOR ZIRCONIUM ALLOYS

BACKGROUND OF THE INVENTION

The invention relates to the field of corrosion testing of zirconium alloys used in nuclear reactors such as pressurized water reactors (PWR) and pressurized heavy water reactors (PHWR) for components and members which are exposed during reactor operation to neutron flux and the hot aqueous coolant under pressure.

Testing in an autoclave of specimens of a zirconium alloy which correspond to the zirconium alloy of actual reactor members is not new. See, for example, U.S. Pat. No. 4,440,862, issued Apr. 3, 1984. The problem of prior art tests has been the required duration, often months and even years, that are required for meaningful results.

Accordingly, it is an important object of the invention to provide an improved short-term autoclave test for ex-reactor evaluation of in-reactor corrosion resistance of zirconium alloy members for use in pressurized water reactors and pressurized heavy water reactors.

In performing the tests, the American Society for Testing Materials (ASTM) "Standard Test Method for Corrosion Testing of Products of Zirconium, Hafnium, and Their Alloys in Water at 680° F. or in Steam at 750° F.," (Designation:G2-88) is used to the extent it is not specifically varied by the claimed procedure. For instance, to insure the simulated coolant is of "low-oxygen", observance by the new procedure of the 45 part per billion oxygen content limit of paragraph 13.1 of G2-88 and venting of the autoclave in the preliminary procedure prior to the actual test (paragraph 14.3) of G2-88, are used.

In order to more quickly measure the corrosion of the specimen and compare the value with values from tests of other specimens to evaluate the in-reactor corrosion resistance of the zirconium alloy member to which the specimen corresponds relative to the in-reactor corrosion resistance of the zirconium alloy members to which the other specimens correspond, it was necessary to establish what happens to cause corrosion of a zirconium alloy member, such as fuel rod cladding tube, in the reactor during operation. A recognition that in-reactor corrosion resistance of zirconium alloys at extended burnups is degraded due to the fracture of hydride precipitates at the metal-oxide interface, has led to an understanding of the reactions in a nuclear reactor.

The aqueous corrosion of zirconium alloys generates hydrogen as a result of the oxidation reaction. A fraction of this generated hydrogen is absorbed by the alloy (metal). When the hydrogen concentration in the metal exceeds the hydrogen solubility limit associated with the corrosion reaction temperature, hydride precipitation occurs. As a result of the volume expansion associated with the oxidation reaction, the corrosion reaction subjects the metal layer to a tensile stress and the oxide layer to a compressive stress. If the hydride precipitates in the metal are brittle at the corrosion temperature, they are unable to withstand the tensile stress generated by the oxidation process and fracture. The fracture of the hydride precipitates disturb the coherency of the metal-oxide interface and renders the oxide sub-layer non-protective. As a result, hydride precipitation enhances the corrosion rate of zirconium alloys. This type of acceleration of corrosion rate occurs in low-oxygen coolant nuclear reactors and was not recognized by earlier investigations. This discovery of the corrosion rate enhancement for zirconium alloys due to hydride precipitation and subsequent fracture forms the basis of the current invention.

Hydrogen has a tendency to migrate towards cooler parts of the zirconium alloy components. Because of imposed heat flux on a fuel cladding in the reactor, the coolest part of the cladding is adjacent to the barrier oxide layer. As a result, the hydrides are concentrated next to the barrier layer. This is not the case for inreactor components without an imposed heat flux or in isothermal autoclave operation where hydrides are uniformly distributed in the cross-section.

The zirconium hydride is a brittle phase at temperatures lower than 427° C. and above this temperature the zirconium hydride phase exhibits some ductility. Therefore, for metal-oxide interface temperatures less than 427° C., the brittle zirconium hydride phase cannot withstand the tensile strain imposed on the substrate metal by the newly forming zirconium oxide (Zr to $ZrO_2$ reaction involves a 56% expansion) and the hydride fractures. Such fracture of zirconium hydride destroys the coherency at the metal-oxide interface, thereby, decreases the "protective" nature of the barrier oxide layer which results in an increased corrosion rate. This is probably the reason for the enhanced in-PWR corrosion observed with hydrogen uptake close to the solubility limit, the "thick-film" hypothesis proposed by Johnson in D. D. Lanning, A. B. Johnson, Jr., D. J. Trimble and S. M. Boyd, "Corrosion and Hydriding of N Reactor Pressure Tubes", Zirconium in the Nuclear Industry: Eighth International Symposium, ASTM STP 1023, L. F. P. Van Swam and C. M. Eucken Eds., American Society for Testing and Materials, Philadelphia, 1989, pp 3–19.

For metal-oxide interface temperatures greater than 427° C., the hydride phase is ductile and with increasing temperatures it can withstand the strains imposed by the oxide layer more effectively. Therefore, zirconium hydride precipitates are not principal reasons for corrosion rate enhancement at higher temperatures (>427° C.).

The long term (>300 days) rate transition observed in prior art autoclave corrosion tests is also related to the hydride precipitation. However, due to the absence of the heat flux, hydride precipitation does not preferentially occur near the metal-oxide interface. Accordingly, long autoclave times are necessary to charge the entire tube wall cross-section to observe the effect of brittle hydrides on the coherency of the metal-oxide interface.

SUMMARY OF THE INVENTION

All of the above has led to a realization by the inventor of three conditions in the reactor to be duplicated ex-reactor for a valid short-term test of zirconium alloy members such as fuel cladding tubes: First, a preferential precipitation of hydrides at the metal-oxide interface where the new oxide is being formed; second, a metal-oxide interface temperature in the autoclave below 427° C., so that the hydrides are brittle and are able to disturb the coherency of the metal-oxide interface to create the same phenomenon as is present during the in-reactor exposure; third, to maintain the coolant in the water phase rather than the steam phase since the effect of alloying elements and manufacturing history on the corrosion resistance are different under water and steam environments. For PWR and PHWR applications, the corrosion data generated in the water phase are applicable.

Realizing this, the invention test procedure has been effectively speeded-up over prior art testing procedures by:

a) a resistance heater placed in the specimen tube portion of cladding material to provide the heat flux necessary to initiate hydride precipitation close to the metal-oxide interface of the tube outside surface;

b) a limited access of water (without significant coolant flow) to the inside (opposing) surface of the tube so that hydrogen charging occurs from both the outer and inner surfaces of the tube such that a lack of significant flow in the gap between the heater and tube inside surface prevents significant cooling of the tube inside surface so that tube inside surface remains at higher temperature than the tube outer surface;

c) a smaller wall thickness of the specimen to attain hydrogen concentration greater than the solubility limit in short exposure time and thereby initiate precipitation of hydrides, thus increasing the corrosion rate;

d) regulation of the autoclave coolant flow and power to produce, as close as possible, the optimum saturation condition of a temperature of 360° C.±5° C. and pressure of 2700 p.s.i.±100 p.s.i. (18.616±0.689 megapascals); the saturation conditions are attained for a better control of the test conditions. The corrosion specimen, however, remains completely in water portion of the autoclave;

e) providing a coolant chemistry substantially the same as in the in-reactor environment;

f) removing most of the dissolved oxygen from the water, i.e., as close to 1 part per billion as possible, but clearly under 45 parts per billion by means of ASTM G2-88, paragraph 14.3 venting.

Utilizing the procedural parameters thus realized, the invention provides an improved short term autoclave corrosion test for zirconium alloys used in PWRs and PHWRs.

The procedure involves providing an autoclave, a flow of low-oxygen (under 45 p.p.b.) coolant having substantially the same aqueous chemistry as would be present in the reactor in which the members being evaluated would be used. The flow is introduced at a temperature in the range of from approximately 300° C. to approximately 365° C. as a substantially saturated liquid within the range of from approximately 1550 p.s.i. (10.687 megapascals) to approximately 2800 p.s.i. (19.305 megapascals). In performing the test, the flow is directed at one of two opposing surfaces of a zirconium alloy specimen corresponding to a member to be evaluated and the other opposed surface is provided limited access to the coolant such that a heat flux exists between the opposing surfaces of the specimen with the surface exposed to the coolant flow at a lower temperature. The corrosion of the specimen is measured and compared to the value with values from tests of other specimens to evaluate the in-reactor corrosion resistance of the zirconium alloy member to which the specimen corresponds relative to the in-reactor corrosion resistance of the zirconium alloy members to which the other specimens correspond. The heat flux between the opposing surfaces of the specimen is preferably enhanced by an electric heater in the tube interior to insure the inner surface is the hotter of the two opposing surfaces.

DESCRIPTION OF THE PREFERRED EMBODIMENT

Figures 1, 2, 3:
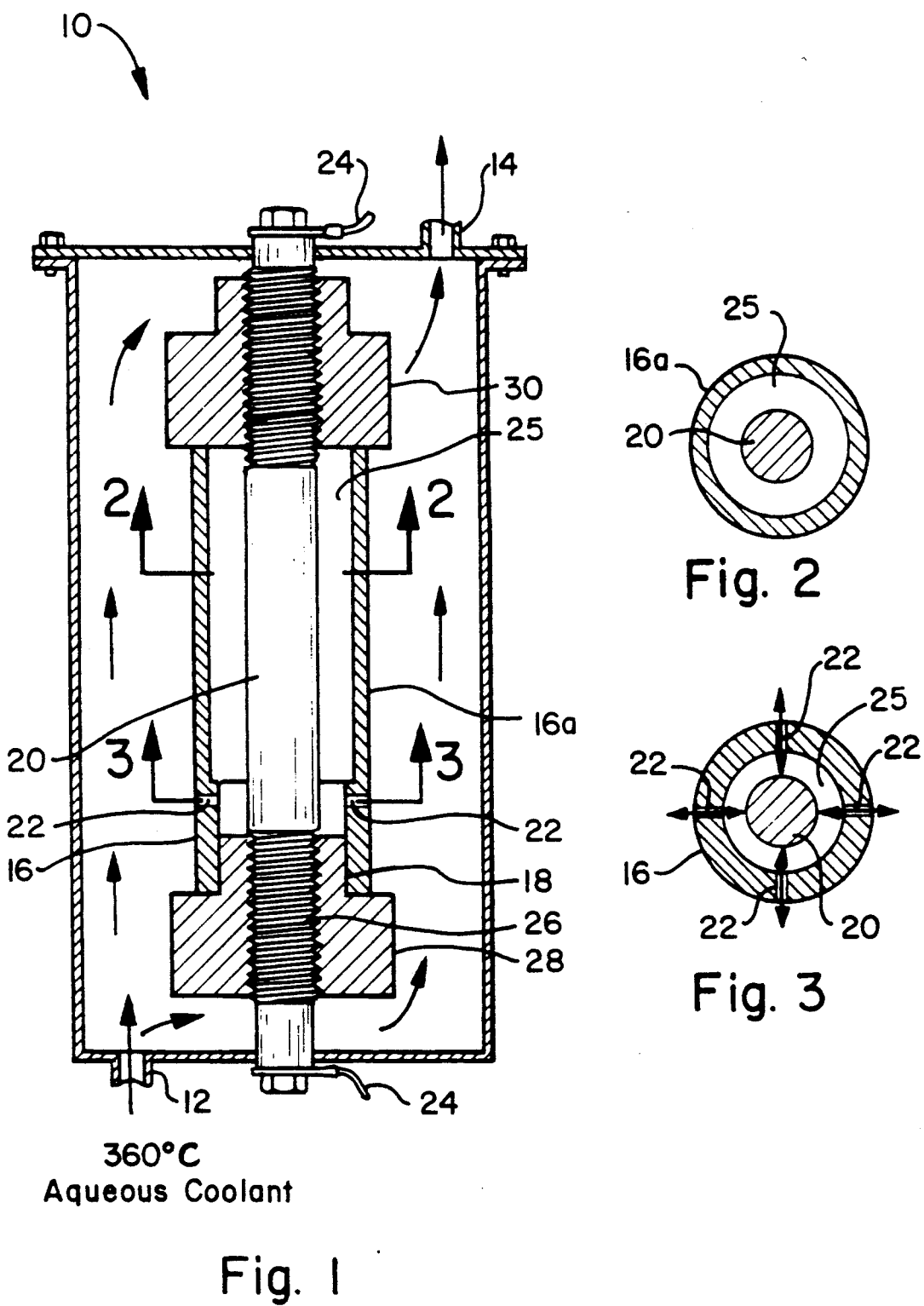
FIG. 1 is a schematic elevational cross-sectional view of an autoclave having a flow of low-oxygen 360° C.±5° C. aqueous coolant in an optimum saturation condition of 2700 p.s.i. +100 p.s.i. (18.616±0.689 megapascals) and coolant chemistry substantially the same as in the in-reactor environment with a zirconium alloy tube portion specimen setup in accordance with the principles of the invention.
FIG. 2 is a cross-sectional view taken along the line 2—2 of FIG. 1.
FIG. 3 is a cross-sectional view taken along the line 3—3 of FIG. 1.

The numeral 10 generally designates the autoclave in which, by use of the principles of the invention, a short-term corrosion test for zirconium alloys to evaluate their corrosion resistance in nuclear reactors such as PWRs and PHWRs with low-oxygen coolants can be accomplished.

The tests of the prior art, for example, a three day test at 400° C., which are currently employed to assess the zirconium alloy material acceptability, are unable to evaluate the long-term extended burnup corrosion resistance of these alloys in nuclear reactors with low oxygen coolant conditions. Long-term isothermal autoclave tests may show an acceleration in corrosion rate at long times (~300 days) that might correlate with the in-reactor corrosion resistance of the alloy. However, long-test duration (~300 days) are necessary. Moreover, the autoclave test temperature (normally between 300° to 500° C.) and medium (steam or water) affects the results. As compared to the in-reactor corrosion behavior, the effect of a change in a particular test or material variable may have an opposite effect on the extent of corrosion depending on the temperature and test medium of a test. While the 500° C. steam test results appear to correlate with in-BWR corrosion resistance, autoclave test conditions suitable for evaluating in-PWR corrosion resistance of Zirconium alloys are not clearly identified in the literature.

The new corrosion test (360° C. water under heat flux conditions with appropriate void fraction and water chemistry) proposed by this invention includes a suitable heat removal arrangement and provides results that will show better correlation with in-PWR or in-PHWR corrosion resistance of zirconium alloys.

The key elements of the new autoclave procedure are to duplicate three conditions in the autoclave that significantly influence the in-reactor fuel cladding corrosion behavior a) preferential precipitation of hydrides at the metal-oxide interface where the new oxide is being formed; b) maintenance of the metal-oxide temperature in the autoclave below ~427° C., so that the hydrides are brittle and are able to disturb the coherency of the metal-oxide interface as they do during the in-reactor exposure; and c) conducting the corrosion test in water (and not steam) environment.

As seen in FIG. 1 schematically, an autoclave inlet port 12 introduces a flow of the 360° C.±5° C. low-oxygen (under 45 p.p.b.) aqueous coolant into the autoclave which exits through an outlet port 14. The controls permit maintenance of the flow at an optimum saturation condition of 2700 p.s.i.±100 p.s.i. (18.616±0.689 megapascals). The flow temperature can be in the range of from approximately 300° C. to approximately 365° C. as a substantially saturated liquid with pressure within the range of from approximately 1550 p.s.i. (10.687 megapascals) to approximately 2800 p.s.i. (19.305 megapascals) but the optimum conditions are preferred.

The specimen is a zirconium alloy tube portion 16 to be tested. It typically will have metallurgy which corresponds to fuel tube cladding such as "Zircaloy 4" or commercial modifications thereof. (See, U.S. Pat. No. 4,440,862 cited above.)

One end of the tube specimen 16 is provided with a plug 18 to install an internal resistance heater 20 concentrically within the specimen. Holes 22 are drilled (for example four holes 90° apart as shown in FIG. 3) at one end of the specimen 16 to permit access of water to the inside surface of the tube without a significant flow of water. This develops the heat flux by making the inside surface hotter than the outside surface which is exposed directly to the flow rather than indirectly to the coolant through holes 22. The holes 22 are also useful as aid in the removal of the specimen from the heater after each corrosion cycle. The power to the heater through conductors 24 and the extent of coolant flow on the tube specimen 16's outer surface are regulated to achieve appropriate void fraction, applicable to the in-reactor conditions under consideration at the cladding tube outer surface.

The corrosion rate in the autoclave test is accelerated by using a specimen wall thickness portion 16a significantly smaller than the wall thickness employed for the fuel cladding. A smaller wall thickness results in a higher precipitation of hydrides and thereby the corrosion rate is increased. It is preferred that no change in manufacture of the member or specimen is made to reduce the thickness of portion 16a but rather material is removed, as by etching on the inside surface only, or some other process which does not disturb the opposed surface of the specimen exposed to flow i.e., the outside surface of specimen 16. This will insure that the specimen surface of interest, the outside surface, will closely correlate to an actual reactor member outside surface.

The resistance heater 20 is inserted in tie specimen 16 of the cladding material to be evaluated. The gap 25 between the heater surface and the tube inside surface is controlled to regulate the heat transfer conditions and to permit water presence at the inside tube surface so that hydrogen charging also occurs at the tube inside surface. The heater/specimen interface is designed in such a way so that repeated removal of specimen after each corrosion test cycle for weight gain measurements is possible without damaging the oxide layer. This is because the heater 20 is threaded, as at 26, to an interior hollow plug member 28 at the lower end of the tube portion 16 and the specimen 16 is seated against an internally threaded end cap 30 at the upper end of the tube portion 16.

The coolant chemistry is consistent with the in-reactor environment. For example, for the PWR case, appropriate lithium and boron additions to the autoclave water are necessary. The condition of the autoclave atmosphere is saturated water. The water having been degassed as explained above to remove the dissolved oxygen by normal techniques at the beginning of each corrosion test cycle.

In order to accelerate the corrosion rate in the autoclave test, the wall thickness portion 16a of the specimen, typically, is reduced to 50% of the original wall thickness of a fuel cladding tube. The reduced wall thickness will enhance the rate of hydrogen charging and thereby promote early precipitation of hydrides in the tube cross-section. The hydrogen transport due to the applied heat flux will result in precipitation of hydrides at the outer metal-oxide interface and thereby the corrosion rate will be enhanced.

The duration of the test will vary according to the corrosion resistance of the material. The corrosion weight gain data are plotted as a function of the autoclave exposure time. The time required for the long-term autoclave corrosion rate acceleration is related to the in-reactor corrosion performance of the cladding material. Therefore, the test duration should be longer than the time required for the long-term transition. An initial estimate of 150 days appears adequate to detect the long-term transition to the accelerated corrosion rate.

A fraction of the amount of hydrogen generated by the aqueous corrosion reaction diffuses through the barrier layer and reacts with zirconium. After exceeding the hydrogen solubility in zirconium, which is limited to about 60 ppm at $\sim 300°$ C., the reactor operating temperature, zirconium hydrides are precipitated. Hydrogen has a tendency to migrate towards cooler parts of the zirconium alloy components. Because of imposed heat flux in the reactor, the coolest part of the cladding is adjacent to the outer surface barrier oxide layer. As a result, the hydrides are concentrated next to the barrier layer. This is not the case in isothermal autoclave operation and hydrides in that case are uniformly distributed across the cladding wall.

The zirconium hydride is a brittle phase at temperatures lower than $\sim 427°$ C. and above this temperature the zirconium hydride phase exhibits some ductility. Therefore, for metal-oxide interface temperatures less than $\sim 427°$ C., the brittle zirconium hydride phase cannot withstand the tensile strain imposed on the substrate metal by the newly forming zirconium oxide (Zr to $ZrO_2$ reaction involves a 56% expansion) and the hydride fractures. Such fracture of zirconium hydride destroys the coherency at the metal-oxide interface, thereby, decreasing the "protective" nature of the barrier oxide layer which results in an increased corrosion rate. Thus, it will be seen that to maintain the brittleness of hydrides (as brittle hydrides affect the in-reactor corrosion rate) and to maintain the water environment it is necessary to utilize 360° C.±5° C. as the highest temperature used to accelerate the corrosion test without jeopardizing the hydride brittleness or entering into the steam phase. Moreover, the hydride precipitation needs to be close to the metal-oxide interface to see the influence on corrosion rate in short duration tests. Also, since the hydrogen adsorption on the oxide surface is a function of void fraction, it is important to achieve the same void fraction as is expected in a PWR. For a low temperature low duty cycle PWR, the void fraction may be zero. For a high temperature, high duty cycle PWR, the applicable void fraction may typically be as high as 5%.

I claim:

1. A short-term autoclave test for ex-reactor evaluation of in-reactor corrosion resistance of zirconium alloy members for use in pressurized water reactors and pressurized heavy water reactors, said test comprising the combination of steps of:

providing in an autoclave, a flow of low-oxygen coolant having substantially the same aqueous chemistry as would be present in the reactor in which the zirconium alloy members being evaluated would be used;

said flow being introduced at a temperature in the range of from approximately 300° C. to approximately 365° C. as a substantially saturated liquid within the range of from approximately 1550 p.s.i. to approximately 2800 p.s.i.;

providing the zirconium alloy specimen containing at least two opposing surfaces;

subjecting one of said two opposing surfaces of a zirconium alloy specimen corresponding to a member to be evaluated to said flow wherein the flow is liquid and the specimen opposing surface other than the one subjected to the flow is exposed to the coolant from the flow but not in the flow;

providing a heat flux between the opposing surfaces of said specimen such that the surface exposed to the coolant flow is at a lower temperature; and, measuring the corrosion of the specimen.

2. The test of claim 1 in which the flow is introduced at a temperature of 360° C. plus or minus 5° C.

3. The test of claim 1 in which the substantially saturated liquid is at a pressure of approximately 2700 p.s.i. plus or minus 100 p.s.i.

4. The test of claim 1 in which the oxygen content of the coolant does not exceed 45 parts per billion.

5. The test of claim 1 in which the opposing surfaces of the specimen are provided at a distance from each other which is less than the distance of corresponding opposing surfaces of the zirconium alloy member being evaluated.

6. The test of claim 1 in which the measuring of the corrosion is by determining the weight gain per unit area.

7. The test of claim 1 in which the specimen is a tube portion.

8. The test of claim 5 in which the specimen is a tube portion and the surface subjected to the flow is the tube portion outer surface and the surface other than the one subjected to the flow is the tube portion inner surface which is in fluid communication with the flow through restrictive holes.

9. The test of claim 5 in which the zirconium alloy member being evaluated for corrosion resistance through use of a corresponding specimen is a nuclear fuel cladding tube and the corresponding specimen is a tube portion of the same zirconium alloy with a thinned wall portion.

10. The test of claim 1 in which the zirconium alloy member being evaluated for corrosion resistance through use of a corresponding specimen is a nuclear fuel cladding tube and the corresponding specimen is a tube portion of the same zirconium alloy which has the heat flux between the opposing surfaces of the specimen enhanced by an electric heater in the tube portion interior to insure the inner surface is the hotter of the two opposing surfaces.

11. The test of claim 1 in which the electric heater is spaced from the inner wall of the tube portion and is exposed to liquid from the flow but not in the flow and in fluid communication with the flow through restrictive holes in the specimen.

* * * * *